(12) United States Patent
Ito et al.

(10) Patent No.: US 7,300,776 B2
(45) Date of Patent: Nov. 27, 2007

(54) L-AMINO ACID-PRODUCING BACTERIUM AND A METHOD FOR PRODUCING L-AMINO ACID

(75) Inventors: Hisao Ito, Kawasaki (JP); Yuji Joe, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/113,270

(22) Filed: Apr. 25, 2005

(65) Prior Publication Data

US 2005/0260720 A1 Nov. 24, 2005

(30) Foreign Application Priority Data

Apr. 26, 2004 (JP) .............................. 2004-130088

(51) Int. Cl.
| | | |
|---|---|---|
| C12P 13/04 | (2006.01) | |
| C12P 13/24 | (2006.01) | |
| C12P 13/22 | (2006.01) | |
| C12P 13/14 | (2006.01) | |
| C12N 9/10 | (2006.01) | |
| C12N 1/21 | (2006.01) | |
| C07H 21/04 | (2006.01) | |

(52) U.S. Cl. ...................... 435/106; 435/107; 435/108; 435/109; 435/110; 435/193; 435/252.33; 435/470; 536/23.2

(58) Field of Classification Search ................ 435/106, 435/107, 108, 109, 110, 252.33, 193; 536/23.2
See application file for complete search history.

(56) References Cited

U.S. PATENT DOCUMENTS

| | | | |
|---|---|---|---|
| 3,808,101 | A | 4/1974 | Enei et al. |
| 5,998,178 | A | 12/1999 | Hashiguchi et al. |
| 6,180,373 | B1 * | 1/2001 | Wich et al. ................. 435/108 |
| 6,653,111 | B2 | 11/2003 | Debabov et al. |
| 7,045,320 | B2 * | 5/2006 | Iwatani et al. .............. 435/108 |
| 2002/0037562 | A1 | 3/2002 | Livshits et al. |
| 2002/0160461 | A1 | 10/2002 | Nakai et al. |
| 2003/0077764 | A1 | 4/2003 | Tsujimoto et al. |
| 2004/0121428 | A1 | 6/2004 | Sugimoto et al. |

FOREIGN PATENT DOCUMENTS

| | | |
|---|---|---|
| EP | 0 488 424 | 6/1992 |
| EP | 1 149 911 | 10/2001 |
| EP | 1 225 230 | 7/2002 |
| EP | 1 352 966 | 10/2003 |
| WO | WO96/14422 | 5/1996 |

OTHER PUBLICATIONS

Wek, R. C., et al., "Rho-dependent Transcriptional Polarity in the ilvGMEDA Operon of Wild-type Escherichia coli K12," J. Biol. Chem. 1987;262(31):15256-15261.
International Search Report for PCT App. No. PCT/JP2005/008402 (Nov. 25, 2005).
Andersen, D. C., et al., "Metabolic Oscillations in an E. coli Fermentation," Biotech. Bioeng. 2001;75(2):212-218.
Lawther, R. P., et al., "Molecular basis of valine resistance in Escherichia coli K-12," Proc. Natl. Acad. Sci. USA 1981;78(2):922-925.
Lawther, R. P., et al., "DNA Sequence Fine-Structure Analysis of ilvG (IlvG+) Mutations of Escherichia coli K-12," J. Bacteriol. 1982;149(1):294-298.
Parekh, B. S. et al., "Growth Rate-Related Regulation of the ilvGMEDA Operon of Escherichia coli K-12 Is a Consequence of the Polar Frameshift Mutation in the ilvG Gene of This Strain," J. Bacteriol. 1997;179(6):2086-2088.
Umbarger, H. E., et al., "Biosynthesis of the Branched-Chain Amino Acids," Escherichia coli and Salmonella, Cellular and Microbiology, (Editors: Neidhardt, F.C., et al.), vol. 1, pp. 442-455, 1996, ASM Press, Washington, DC.
International Preliminary Report on Patentability for PCT Patent App. No. PCT/JP2005/008402 (Nov. 9, 2006).

* cited by examiner

Primary Examiner—Rebecca E. Prouty
Assistant Examiner—Iqbal Chowdhury
(74) Attorney, Agent, or Firm—Shelly Guest Cermak; Cermak Kenealy & Vaidya LLP

(57) ABSTRACT

An L-amino acid-producing strain of Escherichia coli is bred by modifying an Escherichia coli K12 strain or a derivative thereof so as to become resistant to L-valine and have an ability to produce one or more L-amino acids selected from the group consisting of L-tryptophan, L-phenylalanine, L-lysine, L-tyrosine, L-glutamic acid, L-histidine, L-cysteine, and L-proline.

20 Claims, 1 Drawing Sheet

SEQUENCE LISTING

<160> NUMBER OF SEQ ID NOS: 6

<210> SEQ ID NO 1
<211> LENGTH: 984
<212> TYPE: DNA
<213> ORGANISM: Escherichia coli
<220> FEATURE:
<221> NAME/KEY: CDS
<222> LOCATION: (1)..(984)
<223> OTHER INFORMATION:

<400> SEQUENCE: 1

```
atg aat ggc gca cag tgg gtg gta cat gcg ttg cgg gca cag ggt gtg      48
Met Asn Gly Ala Gln Trp Val Val His Ala Leu Arg Ala Gln Gly Val
1               5                   10                  15 aac acc gtt ttc ggt tat ccg ggt ggc gca att atg ccg gtt tac gat      96
Asn Thr Val Phe Gly Tyr Pro Gly Gly Ala Ile Met Pro Val Tyr Asp
            20                  25                  30 gca ttg tat gac ggc ggc gtg gag cac ttg cta tgc cga cat gag cag     144
Ala Leu Tyr Asp Gly Gly Val Glu His Leu Leu Cys Arg His Glu Gln
        35                  40                  45 ggt gcg gca atg gcg gct atc ggt tat gct cgt gct acc ggc aaa act     192
Gly Ala Ala Met Ala Ala Ile Gly Tyr Ala Arg Ala Thr Gly Lys Thr
    50                  55                  60 ggc gta tgt atc gcc acg tct ggt ccg ggc gca acc aac ctg ata acc     240
```

```
                                                                                     -continued Gly Val Cys Ile Ala Thr Ser Gly Pro Gly Ala Thr Asn Leu Ile Thr
 65                  70                  75                  80 ggg ctt gcg gac gca ctg tta gat tcc atc cct gtt gtt gcc atc acc            288
Gly Leu Ala Asp Ala Leu Leu Asp Ser Ile Pro Val Val Ala Ile Thr
                 85                  90                  95 ggt caa gtg tcc gca ccg ttt atc ggc act gac gca ttt cag gaa gtg            336
Gly Gln Val Ser Ala Pro Phe Ile Gly Thr Asp Ala Phe Gln Glu Val
            100                 105                 110 gat gtc ctg gga ttg tcg tta gcc tgt acc aag cac agc ttt ctg gtg            384
Asp Val Leu Gly Leu Ser Leu Ala Cys Thr Lys His Ser Phe Leu Val
        115                 120                 125 cag tcg ctg gaa gag ttg ccg cgc atc atg gct gaa gca ttc gac gtt            432
Gln Ser Leu Glu Glu Leu Pro Arg Ile Met Ala Glu Ala Phe Asp Val
    130                 135                 140 gcc tgc tca ggt cgt cct ggt ccg gtt ctg gtc gat atc cca aaa gat            480
Ala Cys Ser Gly Arg Pro Gly Pro Val Leu Val Asp Ile Pro Lys Asp
145                 150                 155                 160 atc cag tta gcc agc ggt gac ctg gaa ccg tgg ttc acc acc gtt gaa            528
Ile Gln Leu Ala Ser Gly Asp Leu Glu Pro Trp Phe Thr Thr Val Glu
                165                 170                 175 aac gaa gtg act ttc cca cat gcc gaa gtt gag caa gcg cgc cag atg            576
Asn Glu Val Thr Phe Pro His Ala Glu Val Glu Gln Ala Arg Gln Met
            180                 185                 190 ctg gca aaa gcg caa aaa ccg atg ctg tac gtt ggc ggt ggc gtg ggt            624
Leu Ala Lys Ala Gln Lys Pro Met Leu Tyr Val Gly Gly Gly Val Gly
        195                 200                 205 atg gcg cag gca gtt ccg gct ttg cgt gaa ttt ctc gct gcc aca aaa            672
Met Ala Gln Ala Val Pro Ala Leu Arg Glu Phe Leu Ala Ala Thr Lys
    210                 215                 220 atg cct gcc acc tgt acg ctg aaa ggg ctg ggc gca gta gaa gca gat            720
Met Pro Ala Thr Cys Thr Leu Lys Gly Leu Gly Ala Val Glu Ala Asp
225                 230                 235                 240 tat ccg tac tat ctg ggc atg ctg ggg atg cac ggc acc aaa gcg gca            768
Tyr Pro Tyr Tyr Leu Gly Met Leu Gly Met His Gly Thr Lys Ala Ala
                245                 250                 255 aac ttc gcg gtg cag gag tgt gac ctg ctg atc gcc gtg ggc gca cgt            816
Asn Phe Ala Val Gln Glu Cys Asp Leu Leu Ile Ala Val Gly Ala Arg
            260                 265                 270 ttt gat gac cgg gtg acc ggc aaa ctg aac acc ttc gcg cca cac gcc            864
Phe Asp Asp Arg Val Thr Gly Lys Leu Asn Thr Phe Ala Pro His Ala
        275                 280                 285 agt gtt atc cat atg gat atc gac ccg gca gaa atg aac aag ctg cgt            912
Ser Val Ile His Met Asp Ile Asp Pro Ala Glu Met Asn Lys Leu Arg
    290                 295                 300 cag gca cat gtg gca tta caa ggt gat tta aat gct ctg tta cca gca            960
Gln Ala His Val Ala Leu Gln Gly Asp Leu Asn Ala Leu Leu Pro Ala
305                 310                 315                 320 tta cag cag ccg tta aat caa tga                                            984
Leu Gln Gln Pro Leu Asn Gln
                325

<210> SEQ ID NO 2
<211> LENGTH: 327
<212> TYPE: PRT
<213> ORGANISM: Escherichia coli

<400> SEQUENCE: 2

Met Asn Gly Ala Gln Trp Val Val His Ala Leu Arg Ala Gln Gly Val
 1               5                  10                  15

Asn Thr Val Phe Gly Tyr Pro Gly Gly Ala Ile Met Pro Val Tyr Asp
```

-continued

```
                    20                  25                  30
Ala Leu Tyr Asp Gly Gly Val Glu His Leu Leu Cys Arg His Glu Gln
             35                  40                  45

Gly Ala Ala Met Ala Ala Ile Gly Tyr Ala Arg Ala Thr Gly Lys Thr
 50                  55                  60

Gly Val Cys Ile Ala Thr Ser Gly Pro Gly Ala Thr Asn Leu Ile Thr
 65                  70                  75                  80

Gly Leu Ala Asp Ala Leu Leu Asp Ser Ile Pro Val Val Ala Ile Thr
                 85                  90                  95

Gly Gln Val Ser Ala Pro Phe Ile Gly Thr Asp Ala Phe Gln Glu Val
                100                 105                 110

Asp Val Leu Gly Leu Ser Leu Ala Cys Thr Lys His Ser Phe Leu Val
                115                 120                 125

Gln Ser Leu Glu Glu Leu Pro Arg Ile Met Ala Glu Ala Phe Asp Val
         130                 135                 140

Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                 165                 170                 175

Asn Glu Val Thr Phe Pro His Ala Glu Val Glu Gln Ala Arg Gln Met
                180                 185                 190

Leu Ala Lys Ala Gln Lys Pro Met Leu Tyr Val Gly Gly Gly Val Gly
         195                 200                 205

Met Ala Gln Ala Val Pro Ala Leu Arg Glu Phe Leu Ala Ala Thr Lys
 210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                 245                 250                 255

Asn Phe Ala Val Gln Glu Cys Asp Leu Leu Ile Ala Val Gly Ala Arg
                 260                 265                 270

Phe Asp Asp Arg Val Thr Gly Lys Leu Asn Thr Phe Ala Pro His Ala
         275                 280                 285

Ser Val Ile His Met Asp Ile Asp Pro Ala Glu Met Asn Lys Leu Arg
 290                 295                 300

Gln Ala His Val Ala Leu Gln Gly Asp Leu Asn Ala Leu Leu Pro Ala
305                 310                 315                 320

Leu Gln Gln Pro Leu Asn Gln
                 325

<210> SEQ ID NO 3
<211> LENGTH: 1647
<212> TYPE: DNA
<213> ORGANISM: Escherichia coli
<220> FEATURE:
<221> NAME/KEY: CDS
<222> LOCATION: (1)..(1647)
<223> OTHER INFORMATION:

<400> SEQUENCE: 3 atg aat ggc gca cag tgg gtg gta cat gcg ttg cgg gca cag ggt gtg      48
Met Asn Gly Ala Gln Trp Val Val His Ala Leu Arg Ala Gln Gly Val
1               5                  10                  15 aac acc gtt ttc ggt tat ccg ggt ggc gca att atg ccg gtt tac gat      96
Asn Thr Val Phe Gly Tyr Pro Gly Gly Ala Ile Met Pro Val Tyr Asp
             20                  25                  30
```

-continued

| | | |
|---|---|---|
| gca ttg tat gac ggc ggc gtg gag cac ttg cta tgc cga cat gag cag<br>Ala Leu Tyr Asp Gly Gly Val Glu His Leu Leu Cys Arg His Glu Gln<br>35           40                  45 | 144 |
| ggt gcg gca atg gcg gct atc ggt tat gct cgt gct acc ggc aaa act<br>Gly Ala Ala Met Ala Ala Ile Gly Tyr Ala Arg Ala Thr Gly Lys Thr<br>50              55                  60 | 192 |
| ggc gta tgt atc gcc acg tct ggt ccg ggc gca acc aac ctg ata acc<br>Gly Val Cys Ile Ala Thr Ser Gly Pro Gly Ala Thr Asn Leu Ile Thr<br>65              70                  75                  80 | 240 |
| ggg ctt gcg gac gca ctg tta gat tcc atc cct gtt gtt gcc atc acc<br>Gly Leu Ala Asp Ala Leu Leu Asp Ser Ile Pro Val Val Ala Ile Thr<br>              85                  90                  95 | 288 |
| ggt caa gtg tcc gca ccg ttt atc ggc act gac gca ttt cag gaa gtg<br>Gly Gln Val Ser Ala Pro Phe Ile Gly Thr Asp Ala Phe Gln Glu Val<br>              100                 105                 110 | 336 |
| gat gtc ctg gga ttg tcg tta gcc tgt acc aag cac agc ttt ctg gtg<br>Asp Val Leu Gly Leu Ser Leu Ala Cys Thr Lys His Ser Phe Leu Val<br>              115                 120                 125 | 384 |
| cag tcg ctg gaa gag ttg ccg cgc atc atg gct gaa gca ttc gac gtt<br>Gln Ser Leu Glu Glu Leu Pro Arg Ile Met Ala Glu Ala Phe Asp Val<br>130             135                 140 | 432 |
| gcc tgc tca ggt cgt cct ggt ccg gtt ctg gtc gat atc cca aaa gat<br>Ala Cys Ser Gly Arg Pro Gly Pro Val Leu Val Asp Ile Pro Lys Asp<br>145             150                 155                 160 | 480 |
| atc cag tta gcc agc ggt gac ctg gaa ccg tgg ttc acc acc gtt gaa<br>Ile Gln Leu Ala Ser Gly Asp Leu Glu Pro Trp Phe Thr Thr Val Glu<br>              165                 170                 175 | 528 |
| aac gaa gtg act ttc cca cat gcc gaa gtt gag caa gcg cgc cag atg<br>Asn Glu Val Thr Phe Pro His Ala Glu Val Glu Gln Ala Arg Gln Met<br>              180                 185                 190 | 576 |
| ctg gca aaa gcg caa aaa ccg atg ctg tac gtt ggc ggt ggc gtg ggt<br>Leu Ala Lys Ala Gln Lys Pro Met Leu Tyr Val Gly Gly Gly Val Gly<br>              195                 200                 205 | 624 |
| atg gcg cag gca gtt ccg gct ttg cgt gaa ttt ctc gct gcc aca aaa<br>Met Ala Gln Ala Val Pro Ala Leu Arg Glu Phe Leu Ala Ala Thr Lys<br>              210                 215                 220 | 672 |
| atg cct gcc acc tgt acg ctg aaa ggg ctg ggc gca gta gaa gca gat<br>Met Pro Ala Thr Cys Thr Leu Lys Gly Leu Gly Ala Val Glu Ala Asp<br>225             230                 235                 240 | 720 |
| tat ccg tac tat ctg ggc atg ctg ggg atg cac ggc acc aaa gcg gca<br>Tyr Pro Tyr Tyr Leu Gly Met Leu Gly Met His Gly Thr Lys Ala Ala<br>              245                 250                 255 | 768 |
| aac ttc gcg gtg cag gag tgt gac ctg ctg atc gcc gtg ggc gca cgt<br>Asn Phe Ala Val Gln Glu Cys Asp Leu Leu Ile Ala Val Gly Ala Arg<br>              260                 265                 270 | 816 |
| ttt gat gac cgg gtg acc ggc aaa ctg aac acc ttc gcg cca cac gcc<br>Phe Asp Asp Arg Val Thr Gly Lys Leu Asn Thr Phe Ala Pro His Ala<br>              275                 280                 285 | 864 |
| agt gtt atc cat atg gat atc gac ccg gca gaa atg aac aag ctg cgt<br>Ser Val Ile His Met Asp Ile Asp Pro Ala Glu Met Asn Lys Leu Arg<br>              290                 295                 300 | 912 |
| cag gca cat gtg gca tta caa ggt gat tta aat gct ctg tta cca gca<br>Gln Ala His Val Ala Leu Gln Gly Asp Leu Asn Ala Leu Leu Pro Ala<br>305             310                 315                 320 | 960 |
| tta cag cag ccg tta aat caa tgt gac tgg cag caa cac tgc gcg cag<br>Leu Gln Gln Pro Leu Asn Gln Cys Asp Trp Gln Gln His Cys Ala Gln<br>              325                 330                 335 | 1008 |
| ctg cgt gat gaa cat tcc tgg cgt tac gac cat ccc ggt gac gct atc<br>Leu Arg Asp Glu His Ser Trp Arg Tyr Asp His Pro Gly Asp Ala Ile<br>              340                 345                 350 | 1056 |

-continued

```
tac gcg ccg ttg ttg tta aaa caa ctg tcg gat cgt aaa cct gcg gat      1104
Tyr Ala Pro Leu Leu Leu Lys Gln Leu Ser Asp Arg Lys Pro Ala Asp
            355                 360                 365 tgc gtc gtg acc aca gat gtg ggg cag cac cag atg tgg gct gcg cag      1152
Cys Val Val Thr Thr Asp Val Gly Gln His Gln Met Trp Ala Ala Gln
    370                 375                 380 cac atc gcc cac act cgc ccg gaa aat ttc atc acc tcc agc ggt tta      1200
His Ile Ala His Thr Arg Pro Glu Asn Phe Ile Thr Ser Ser Gly Leu
385                 390                 395                 400 ggt acc atg ggt ttt ggt tta ccg gcg gcg gtt ggc gca caa gtc gcg      1248
Gly Thr Met Gly Phe Gly Leu Pro Ala Ala Val Gly Ala Gln Val Ala
                405                 410                 415 cga ccg aac gat acc gtt gtc tgt atc tcc ggt gac ggc tct ttc atg      1296
Arg Pro Asn Asp Thr Val Val Cys Ile Ser Gly Asp Gly Ser Phe Met
            420                 425                 430 atg aat gtg caa gag ctg ggc acc gta aaa cgc aag cag tta ccg ttg      1344
Met Asn Val Gln Glu Leu Gly Thr Val Lys Arg Lys Gln Leu Pro Leu
        435                 440                 445 aaa atc gtc tta ctc gat aac caa cgg tta ggg atg gtt cga caa tgg      1392
Lys Ile Val Leu Leu Asp Asn Gln Arg Leu Gly Met Val Arg Gln Trp
450                 455                 460 cag caa ctg ttt ttt cag gaa cga tac agc gaa acc acc ctt act gat      1440
Gln Gln Leu Phe Phe Gln Glu Arg Tyr Ser Glu Thr Thr Leu Thr Asp
465                 470                 475                 480 aac ccc gat ttc ctc atg tta gcc agc gcc ttc ggc atc cat ggc caa      1488
Asn Pro Asp Phe Leu Met Leu Ala Ser Ala Phe Gly Ile His Gly Gln
                485                 490                 495 cac atc acc cgg aaa gac cag gtt gaa gcg gca ctc gac acc atg ctg      1536
His Ile Thr Arg Lys Asp Gln Val Glu Ala Ala Leu Asp Thr Met Leu
            500                 505                 510 aac agt gat ggg cca tac ctg ctt cat gtc tca atc gac gaa ctt gag      1584
Asn Ser Asp Gly Pro Tyr Leu Leu His Val Ser Ile Asp Glu Leu Glu
        515                 520                 525 aac gtc tgg ccg ctg gtg ccg cct ggc gcc agt aat tca gaa atg ttg      1632
Asn Val Trp Pro Leu Val Pro Pro Gly Ala Ser Asn Ser Glu Met Leu
    530                 535                 540 gag aaa tta tca tga                                                  1647
Glu Lys Leu Ser
545
```

<210> SEQ ID NO 4
<211> LENGTH: 548
<212> TYPE: PRT
<213> ORGANISM: Escherichia coli

<400> SEQUENCE: 4

```
Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Thr
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95
```

-continued

Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
    130                 135                 140

Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Ala Arg Gln Met
            180                 185                 190

Leu Ala Lys Ala Gln Lys Pro Met Leu Tyr Val Gly Gly Gly Val Gly
        195                 200                 205

Met Ala Gln Ala Val Pro Ala Leu Arg Glu Phe Leu Ala Ala Thr Lys
    210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
            260                 265                 270

Phe Asp Asp Arg Val Thr Gly Lys Leu Asn Thr Phe Ala Pro His Ala
        275                 280                 285

Ser Val Ile His Met Asp Ile Asp Pro Ala Glu Met Asn Lys Leu Arg
    290                 295                 300

Gln Ala His Val Ala Leu Gln Gly Asp Leu Asn Ala Leu Leu Pro Ala
305                 310                 315                 320

Leu Gln Gln Pro Leu Asn Gln Cys Asp Trp Gln Gln His Cys Ala Gln
                325                 330                 335

Leu Arg Asp Glu His Ser Trp Arg Tyr Asp His Pro Gly Asp Ala Ile
            340                 345                 350

Tyr Ala Pro Leu Leu Leu Lys Gln Leu Ser Asp Arg Lys Pro Ala Asp
        355                 360                 365

Cys Val Val Thr Thr Asp Val Gly Gln His Gln Met Trp Ala Ala Gln
    370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
            420                 425                 430

Met Asn Val Gln Glu Leu Gly Thr Val Lys Arg Lys Gln Leu Pro Leu
        435                 440                 445

Lys Ile Val Leu Leu Asp Asn Gln Arg Leu Gly Met Val Arg Gln Trp
    450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile His Gly Gln
                485                 490                 495

His Ile Thr Arg Lys Asp Gln Val Glu Ala Ala Leu Asp Thr Met Leu
            500                 505                 510

Asn Ser Asp Gly Pro Tyr Leu Leu His Val Ser Ile Asp Glu Leu Glu

-continued

```
                515                 520                 525
Asn Val Trp Pro Leu Val Pro Pro Gly Ala Ser Asn Ser Glu Met Leu
    530                 535                 540

Glu Lys Leu Ser
545

<210> SEQ ID NO 5
<211> LENGTH: 1644
<212> TYPE: DNA
<213> ORGANISM: Escherichia coli
<220> FEATURE:
<221> NAME/KEY: CDS
<222> LOCATION: (1)..(1644)
<223> OTHER INFORMATION:

<400> SEQUENCE: 5 atg aat ggc gca cag tgg gtg gta cat gcg ttg cgg gca cag ggt gtg      48
Met Asn Gly Ala Gln Trp Val Val His Ala Leu Arg Ala Gln Gly Val
1               5                  10                  15 aac acc gtt ttc ggt tat ccg ggt ggc gca att atg ccg gtt tac gat      96
Asn Thr Val Phe Gly Tyr Pro Gly Gly Ala Ile Met Pro Val Tyr Asp
            20                  25                  30 gca ttg tat gac ggc ggc gtg gag cac ttg cta tgc cga cat gag cag     144
Ala Leu Tyr Asp Gly Gly Val Glu His Leu Leu Cys Arg His Glu Gln
        35                  40                  45 ggt gcg gca atg gcg gct atc ggt tat gct cgt gct acc ggc aaa act     192
Gly Ala Ala Met Ala Ala Ile Gly Tyr Ala Arg Ala Thr Gly Lys Thr
    50                  55                  60 ggc gta tgt atc gcc acg tct ggt ccg ggc gca acc aac ctg ata acc     240
Gly Val Cys Ile Ala Thr Ser Gly Pro Gly Ala Thr Asn Leu Ile Thr
65                  70                  75                  80 ggg ctt gcg gac gca ctg tta gat tcc atc cct gtt gtt gcc atc acc     288
Gly Leu Ala Asp Ala Leu Leu Asp Ser Ile Pro Val Val Ala Ile Thr
                85                  90                  95 ggt caa gtg tcc gca ccg ttt atc ggc act gac gca ttt cag gaa gtg     336
Gly Gln Val Ser Ala Pro Phe Ile Gly Thr Asp Ala Phe Gln Glu Val
            100                 105                 110 gat gtc ctg gga ttg tcg tta gcc tgt acc aag cac agc ttt ctg gtg     384
Asp Val Leu Gly Leu Ser Leu Ala Cys Thr Lys His Ser Phe Leu Val
        115                 120                 125 cag tcg ctg gaa gag ttg ccg cgc atc atg gct gaa gca ttc gac gtt     432
Gln Ser Leu Glu Glu Leu Pro Arg Ile Met Ala Glu Ala Phe Asp Val
    130                 135                 140 gcc tgc tca ggt cgt cct ggt ccg gtt ctg gtc gat atc cca aaa gat     480
Ala Cys Ser Gly Arg Pro Gly Pro Val Leu Val Asp Ile Pro Lys Asp
145                 150                 155                 160 atc cag tta gcc agc ggt gac ctg gaa ccg tgg ttc acc acc gtt gaa     528
Ile Gln Leu Ala Ser Gly Asp Leu Glu Pro Trp Phe Thr Thr Val Glu
                165                 170                 175 aac gaa gtg act ttc cca cat gcc gaa gtt gag caa gcg cgc cag atg     576
Asn Glu Val Thr Phe Pro His Ala Glu Val Glu Gln Ala Arg Gln Met
            180                 185                 190 ctg gca aaa gcg caa aaa ccg atg ctg tac gtt ggc ggt ggc gtg ggt     624
Leu Ala Lys Ala Gln Lys Pro Met Leu Tyr Val Gly Gly Gly Val Gly
        195                 200                 205 atg gcg cag gca gtt ccg gct ttg cgt gaa ttt ctc gct gcc aca aaa     672
Met Ala Gln Ala Val Pro Ala Leu Arg Glu Phe Leu Ala Ala Thr Lys
    210                 215                 220 atg cct gcc acc tgt acg ctg aaa ggg ctg ggc gca gta gaa gca gat     720
Met Pro Ala Thr Cys Thr Leu Lys Gly Leu Gly Ala Val Glu Ala Asp
225                 230                 235                 240
```

```
tat ccg tac tat ctg ggc atg ctg ggg atg cac ggc acc aaa gcg gca       768
Tyr Pro Tyr Tyr Leu Gly Met Leu Gly Met His Gly Thr Lys Ala Ala
            245                 250                 255 aac ttc gcg gtg cag gag tgt gac ctg ctg atc gcc gtg ggc gca cgt       816
Asn Phe Ala Val Gln Glu Cys Asp Leu Leu Ile Ala Val Gly Ala Arg
                260                 265                 270 ttt gat gac cgg gtg acc ggc aaa ctg aac acc ttc gcg cca cac gcc       864
Phe Asp Asp Arg Val Thr Gly Lys Leu Asn Thr Phe Ala Pro His Ala
                    275                 280                 285 agt gtt atc cat atg gat atc gac ccg gca gaa atg aac aag ctg cgt       912
Ser Val Ile His Met Asp Ile Asp Pro Ala Glu Met Asn Lys Leu Arg
        290                 295                 300 cag gca cat gtg gca tta caa ggt gat tta aat gct ctg tta cca gca       960
Gln Ala His Val Ala Leu Gln Gly Asp Leu Asn Ala Leu Leu Pro Ala
305                 310                 315                 320 tta cag cag ccg tta aat aat gac tgg cag caa cac tgc gcg cag ctg      1008
Leu Gln Gln Pro Leu Asn Asn Asp Trp Gln Gln His Cys Ala Gln Leu
                325                 330                 335 cgt gat gaa cat tcc tgg cgt tac gac cat ccc ggt gac gct atc tac      1056
Arg Asp Glu His Ser Trp Arg Tyr Asp His Pro Gly Asp Ala Ile Tyr
                    340                 345                 350 gcg ccg ttg ttg tta aaa caa ctg tcg gat cgt aaa cct gcg gat tgc      1104
Ala Pro Leu Leu Leu Lys Gln Leu Ser Asp Arg Lys Pro Ala Asp Cys
        355                 360                 365 gtc gtg acc aca gat gtg ggg cag cac cag atg tgg gct gcg cag cac      1152
Val Val Thr Thr Asp Val Gly Gln His Gln Met Trp Ala Ala Gln His
370                 375                 380 atc gcc cac act cgc ccg gaa aat ttc atc acc tcc agc ggt tta ggt      1200
Ile Ala His Thr Arg Pro Glu Asn Phe Ile Thr Ser Ser Gly Leu Gly
385                 390                 395                 400 acc atg ggt ttt ggt tta ccg gcg gcg gtt ggc gca caa gtc gcg cga      1248
Thr Met Gly Phe Gly Leu Pro Ala Ala Val Gly Ala Gln Val Ala Arg
                405                 410                 415 ccg aac gat acc gtt gtc tgt atc tcc ggt gac ggc tct ttc atg atg      1296
Pro Asn Asp Thr Val Val Cys Ile Ser Gly Asp Gly Ser Phe Met Met
                    420                 425                 430 aat gtg caa gag ctg ggc acc gta aaa cgc aag cag tta ccg ttg aaa      1344
Asn Val Gln Glu Leu Gly Thr Val Lys Arg Lys Gln Leu Pro Leu Lys
        435                 440                 445 atc gtc tta ctc gat aac caa cgg tta ggg atg gtt cga caa tgg cag      1392
Ile Val Leu Leu Asp Asn Gln Arg Leu Gly Met Val Arg Gln Trp Gln
450                 455                 460 caa ctg ttt ttt cag gaa cga tac agc gaa acc acc ctt act gat aac      1440
Gln Leu Phe Phe Gln Glu Arg Tyr Ser Glu Thr Thr Leu Thr Asp Asn
465                 470                 475                 480 ccc gat ttc ctc atg tta gcc agc gcc ttc ggc atc cat ggc caa cac      1488
Pro Asp Phe Leu Met Leu Ala Ser Ala Phe Gly Ile His Gly Gln His
                485                 490                 495 atc acc cgg aaa gac cag gtt gaa gcg gca ctc gac acc atg ctg aac      1536
Ile Thr Arg Lys Asp Gln Val Glu Ala Ala Leu Asp Thr Met Leu Asn
                    500                 505                 510 agt gat ggg cca tac ctg ctt cat gtc tca atc gac gaa ctt gag aac      1584
Ser Asp Gly Pro Tyr Leu Leu His Val Ser Ile Asp Glu Leu Glu Asn
        515                 520                 525 gtc tgg ccg ctg gtg ccg cct ggc gcc agt aat tca gaa atg ttg gag      1632
Val Trp Pro Leu Val Pro Pro Gly Ala Ser Asn Ser Glu Met Leu Glu
530                 535                 540 aaa tta tca tga                                                      1644
Lys Leu Ser
```

545

<210> SEQ ID NO 6
<211> LENGTH: 547
<212> TYPE: PRT
<213> ORGANISM: Escherichia coli

<400> SEQUENCE: 6

Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Thr
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95

Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
    130                 135                 140

Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Gln Ala Arg Gln Met
            180                 185                 190

Leu Ala Lys Ala Gln Lys Pro Met Leu Tyr Val Gly Gly Gly Val Gly
        195                 200                 205

Met Ala Gln Ala Val Pro Ala Leu Arg Glu Phe Leu Ala Ala Thr Lys
    210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
            260                 265                 270

Phe Asp Asp Arg Val Thr Gly Lys Leu Asn Thr Phe Ala Pro His Ala
        275                 280                 285

Ser Val Ile His Met Asp Ile Asp Pro Ala Glu Met Asn Lys Leu Arg
    290                 295                 300

Gln Ala His Val Ala Leu Gln Gly Asp Leu Asn Ala Leu Leu Pro Ala
305                 310                 315                 320

Leu Gln Gln Pro Leu Asn Asn Asp Trp Gln Gln His Cys Ala Gln Leu
                325                 330                 335

Arg Asp Glu His Ser Trp Arg Tyr Asp His Pro Gly Asp Ala Ile Tyr
            340                 345                 350

Ala Pro Leu Leu Leu Lys Gln Leu Ser Asp Arg Lys Pro Ala Asp Cys
        355                 360                 365

```
-continued

Val Val Thr Thr Asp Val Gly Gln His Gln Met Trp Ala Ala Gln His
    370             375             380

Ile Ala His Thr Arg Pro Glu Asn Phe Ile Thr Ser Ser Gly Leu Gly
385             390             395                     400

Thr Met Gly Phe Gly Leu Pro Ala Ala Val Gly Ala Gln Val Ala Arg
            405             410             415

Pro Asn Asp Thr Val Val Cys Ile Ser Gly Asp Gly Ser Phe Met Met
            420             425             430

Asn Val Gln Glu Leu Gly Thr Val Lys Arg Lys Gln Leu Pro Leu Lys
        435             440             445

Ile Val Leu Leu Asp Asn Gln Arg Leu Gly Met Val Arg Gln Trp Gln
    450             455             460

Gln Leu Phe Phe Gln Glu Arg Tyr Ser Glu Thr Thr Leu Thr Asp Asn
465             470             475             480

Pro Asp Phe Leu Met Leu Ala Ser Ala Phe Gly Ile His Gly Gln His
            485             490             495

Ile Thr Arg Lys Asp Gln Val Glu Ala Ala Leu Asp Thr Met Leu Asn
            500             505             510

Ser Asp Gly Pro Tyr Leu Leu His Val Ser Ile Asp Glu Leu Glu Asn
        515             520             525

Val Trp Pro Leu Val Pro Pro Gly Ala Ser Asn Ser Glu Met Leu Glu
    530             535             540

Lys Leu Ser
545
```

L-AMINO ACID-PRODUCING BACTERIUM AND A METHOD FOR PRODUCING L-AMINO ACID

FIELD OF THE INVENTION

The present invention relates to a method for producing L-amino acids using *Escherichia coli*. In particular, the present invention relates to a method for producing L-tryptophan, L-lysine, L-phenylalanine, L-tyrosine, L-glutamic acid, L-histidine, L-cysteine, or L-proline. These are industrially useful L-amino acids. Namely, L-tryptophan and L-lysine are useful as additives for animal feed, components of health food, and amino acid infusions. L-phenylalanine is useful as animal feed and as a precursor of aspartame. L-tyrosine is useful as a raw material for producing adrenaline. L-glutamic acid is useful as a seasoning material, as an amino acid infusion, and as a component of amino acid preparations. L-histidine is useful as a liver function-promoting drug and as a precursor of histamine. L-cysteine is useful as a food additive, and as a component of pharmaceuticals and cosmetics. L-proline is useful as an amino acid infusion.

BRIEF DESCRIPTION OF THE RELATED ART

Bacteria belonging to the genus *Escherichia* have been used in fermentative production of L-amino acids (Amino Acid Fermentation, Japan Scientific Societies Press, 1986, p. 77 to 84). L-amino acid-producing bacteria used in the fermentative production have been generally bred by modification to enhance an activity of an L-amino acid-biosynthetic enzyme using a recombinant DNA technique or by mutating a bacterial strain to impart L-amino acid-producing ability. For example, one or more mutations have been introduced by treating a strain with a mutagen such as N-methyl-N'-nitro-N-nitrosoguanidine. However, this method sometimes causes problems such as a mutation is introduced into genes other than the target gene, for example, a gene important for growth, thus the mutated strain becomes auxotrophic to some nutrients. On the other hand, when enhancing the activity of the target enzyme in the L-amino acid biosynthetic pathway, only some metabolic pathways are activated, which can result in an energy imbalance and a lack of nutritional substances such as L-amino acids other than the target L-amino acid. In this case, it is necessary to perform the fermentation in a medium supplemented with a nutrient required by the auxotrophic strain. However, this can cause the problem that these nutrients can remain as a contaminate during collection of the target L-amino acid from culture medium.

*Escherichia coli* K12 strain is representative of a strain useful for breeding L-amino acid-producing bacteria. As an L-amino acid-producing bacterium bred from an *Escherichia coli* K12 strain, for example, a mutant strain with an altered metabolic activity and a strain modified so that the activity of an L-amino acid biosynthetic enzyme is enhanced by a recombinant DNA technique has been reported (U.S. Pat. No. 6,653,111 or JP 3185261 B).

The K12 strain is sensitive to L-valine, and its growth is suppressed in a medium containing L-valine. That is, when it is cultured in a medium containing L-valine, its growth is not observed or is delayed as compared with a culture in a medium not containing L-valine. When the strain is cultured in a medium which does not contain L-valine, branched-chain L-amino acids such as L-isoleucine and L-leucine are not produced, resulting in worse growth. Accordingly, in order to prevent worse growth, it is necessary to culture it in a medium containing L-isoleucine and L-leucine, which are classified as branched-chain L-amino acids, like L-valine. However, when producing an L-amino acid other than L-isoleucine or L-leucine, adding L-isoleucine or L-leucine is not preferable.

*Escherichia coli* contains acetohydroxy acid synthase (AHAS), which catalyzes the first step in the biosynthetic pathway of branched-chain L-amino acids. Three isozymes of AHAS exist in *Escherichia coli*: AHASI, AHASII, and AHASIII. The K12 strain has a frameshift mutation in the ilvG gene, which encodes a large subunit of the isozyme AHASII, so that the normal ilvG gene is not expressed (Proc. Natl. Acad. Sci USA, 1981, vol. 78: p 922-925).

It has been reported that by introducing a mutation which imparts L-valine resistance into a K12 strain, expression of a normal ilvG gene is able to be restored (*E. coli* and *Salmonella* 2nd Edition 1996, vol. 1, p 442-457). Moreover, a method for producing L-isoleucine or L-leucine using a K12 strain into which an ilvGMEDA operon containing the ilvG gene without the introduced frameshift mutation has been reported (U.S. Pat. No. 5,998,178 or JP-A 2001-346578). A method for producing L-leucine using a K12 strain imparted with L-valine resistance has been reported (JP-A 2000-116393).

However, using an L-amino acid-producing bacterium derived from a K12 strain, which has been modified to have L-valine resistance or to reverse a frameshift mutation of the ilvG gene for the production of L-tryptophan, L-phenylalanine, L-lysine, L-tyrosine, L-glutamic acid, L-histidine, L-cysteine, and L-proline has never been reported.

SUMMARY OF THE INVENTION

It is an object of the present invention to provide a strain capable of effectively producing an L-amino acid such as L-tryptophan, L-phenylalanine, L-lysine, L-tyrosine, L-glutamic acid, L-histidine, L-cysteine, and L-proline by modifying a K12 strain. It is also an object of the present invention to provide a method of producing the L-amino acids using this strain.

The inventors of the present invention have made extensive studies for achieving the above-described object. As a result, they found that, SV164/pGH5 strain, a derivative strain of K12 strain, produces L-tryptophan more efficiently when a branched-chain L-amino acid is added into a culture medium. Furthermore, they found that an ability of the SV164/pGH5 strain to produce an L-amino acid other than a branched-chain L-amino acid, especially L-tryptophan is improved when L-valine resistance is imparted to the strain by restoring a frameshift mutation of ilvG gene, thereby accomplishing the present invention.

It is an object of the present invention to provide an isolated strain of *Escherichia coli* obtainable by modifying an *Escherichia coli* K12 strain or a derivative thereof, wherein said isolated strain is resistant to L-valine and has an ability to produce one or more L-amino acids selected from the group consisting of L-tryptophan, L-phenylalanine, L-lysine, L-tyrosine, L-glutamic acid, L-histidine, L-cysteine, and L-proline.

It is a further object of the present invention to provide the strain as described above, wherein said strain has an ability to grow in a medium containing 20 mg/L of L-valine.

It is a further object of the present invention to provide the strain as described above, wherein said isolated strain is modified to be L-valine-resistant by enhancing an intracellular acetohydroxy acid synthase activity so that it is higher than that of non-modified K12 strain.

It is a further object of the present invention to provide the strain as described above, wherein said isolated strain is modified so as to produce active acetohydroxy acid synthase II.

It is a further object of the present invention to provide the strain as described above, wherein said active acetohydroxy acid synthase II is a protein encoded by a gene comprising a nucleotide sequence of SEQ ID NO: 3 or 5.

It is a further object of the present invention to provide a method for producing L-tryptophan, L-phenylalanine, L-lysine, L-tyrosine, L-glutamic acid, L-histidine, L-cysteine, or L-proline, comprising culturing the strain as described above in a medium, and collecting L-tryptophan, L-phenylalanine, L-lysine, L-tyrosine, L-glutamic acid, L-histidine, L-cysteine, or L-proline from the medium or bacterial cells.

DETAILED DESCRIPTION OF THE PREFERRED EMBODIMENTS

Figure 1:
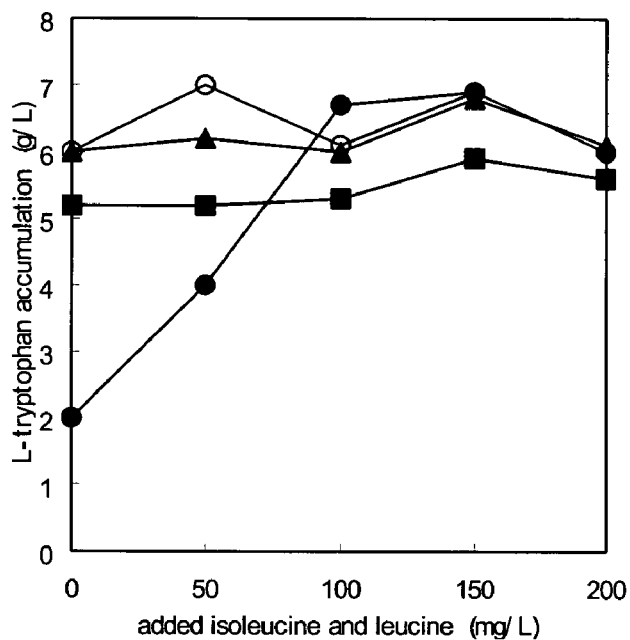
FIG. 1 shows the effect of L-leucine and L-isoleucine on L-tryptophan accumulation by the SV164/pGH5 strain and the L-valine resistant strains. The symbols ●, □, △, and ○ represent SV164/pGH5 strain, M6 strain, M9 strain, and T2 strain, respectively.

Hereinafter, the present invention will be described in detail.

<1> Microorganism of the Present Invention

The microorganism of the present invention is a strain of *Escherichia coli*, which is obtainable by modifying the *Escherichia coli* K12 strain or a derivative thereof to be resistant to L-valine and to have an ability to produce one or more L-amino acids selected from the group consisting of L-tryptophan, L-phenylalanine, L-lysine, L-tyrosine, L-glutamic acid, L-histidine, L-cysteine, and L-proline. The L-amino acids to be produced are preferably aromatic L-amino acids, such as L-tryptophan, L-phenylalanine, and L-tyrosine.

The *Escherichia coli* K12 strain was isolated at Stanford University in 1922 and is a lysogenic bacterium of λ phage. In addition, it is a versatile strain having the F-factor, from which genetic recombinant strains can be constructed by conjugation, gene amplification, or the like. Furthermore, the genomic sequence of *Escherichia coli* K12 strain has been determined, and hence the gene information thereof is available (Science 277 (5331), 1453-1474 (1997)). The *Escherichia coli* K12 strain and derivatives thereof can be obtained from the American Type Culture Collection (ATCC, Address: P.O. Box 1549, Manassas, Va. 20108, United States of America).

A derivative of the K12 strain of the present invention is not particularly limited as long as it has the ilvG gene derived from the K12 strain, i.e., the ilvG gene which has the frameshift mutation described below. Examples thereof include the *Escherichia coli* MG1655 strain (ATCC No. 47076), W3110 strain (ATCC No. 27325), and SV164 strain (JP 3032013 B).

In order to obtain the *Escherichia coli* strain of the present invention, firstly, the above-described K12 strain or a derivative thereof is modified to be resistant to L-valine. The term "resistant to L-valine" means that the strain has an ability to grow in a medium containing a high concentration of L-valine. In the present specification, the term "high concentration" means, for example, 20 mg/L or more, preferably 100 mg/L.

Such a modification can be performed as follows: for example, *Escherichia coli* K12 strain or a derivative thereof is subjected to a mutation treatment, and a strain capable of growing in a medium containing a high concentration of L-valine is selected from the resulting mutant strains. The mutation treatment to obtain an L-valine-resistant strain is not particularly limited, and examples thereof include treating with ultraviolet radiation or treating with a mutagen typically used in such a mutation treatment, such as N-methyl-N'-nitro-N-nitrosoguanidine (NTG) or nitrous acid.

For example, a culture of a mutant strain that has been cultured in a liquid medium until the logarithmic growth phase or stationary phase is diluted with a fresh liquid medium, saline, etc., and the resulting bacterial cell suspension is applied to a solid medium containing L-valine, and is cultured at the optimum growth temperature, for example, at 37° C. for 1 to 3 days. Then, the colonies which appear are selected as L-valine resistant strains. The amount of L-valine which is added to the medium is, for example, 20 mg/L or more, preferably about 100 mg/L.

An example of a medium which can be used for selecting L-valine resistant strains includes a minimum medium. An example of a minimum medium containing L-valine includes a medium having the following composition: 4 g/L glucose, 12.8 g/L disodium hydrogen phosphate, 3 g/L potassium dihydrogen phosphate, 1 g/L sodium chloride, 1 g/L ammonium chloride, 5 mM magnesium sulfate, 0.1 mM calcium chloride, 1 mg/L thiamine, and 20 mg/L L-valine.

The minimum medium may contain a nutrient which is essential for growth, if necessary. For example, when L-valine resistance is imparted to an L-tryptophan-producing mutant strain, the medium preferably contains L-phenylalanine and L-tyrosine in amounts necessary for growth, because most of the L-tryptophan-producing mutant strains have weakened biosynthetic pathways for L-phenylalanine and L-tyrosine and are auxotrophic to L-phenylalanine and L-tyrosine.

Furthermore, L-valine resistance may be imparted by a gene recombination technique. For example, a K12 strain or a derivative thereof may be imparted with L-valine resistance by a modification which enhances intracellular activity of an L-valine biosynthetic enzyme, e.g., acetohydroxy acid synthase, so that it is higher than that of unmodified K12 strain. The activity of acetohydroxy acid synthase can be determined by the method described in Westerferd, W. W (1945) J. Biol. Chem, 161, 495-502.

It is known that three isozymes, AHASI, AHASII, and AHASIII, of acetohydroxy acid synthase (acetolactate synthase) exist in *Escherichia coli*. Of these, AHASII consists of a large subunit and a small subunit, which are encoded by the ilvG and ilvM genes, respectively.

The nucleotide sequence of the ilvG gene from the MG 1655 strain, which is a derivative of *Escherichia coli* K 12 strain, is shown in SEQ ID NO: 1 (GenBank Accession No. AAC77488). As shown in SEQ ID NO: 1, in the ilvG gene from the K12 strain or a derivative thereof, nucleotides GT at positions 983 and 984 of the ilvG gene derived from other strains of *Escherichia coli* (O strain, B strain etc.) (for example, a gene having a nucleotide sequence of SEQ ID NO: 3; hereinafter, referred to as normal ilvG gene) are deleted, so that a frameshift mutation occurs, and nucleotides TGA at positions 982 to 984 of SEQ ID NO: 1 serve as a translation termination codon. For this reason, the normal ilvG gene is not expressed, and the AHASII activity is eliminated in the K12 strain or a derivative thereof.

Accordingly, in order to increase the AHAS activity in the *Escherichia coli* K12 strain or a derivative thereof, the strain is preferably modified to produce active AHASII. For that purpose, the strain is preferably modified so that it harbors the ilvG gene which does not have the frameshift mutation (for example, a gene having the nucleotide sequence of SEQ ID NO: 3 or 5). Specifically, a gene in which the TGA at position 982 to 984 of the ilvG gene of SEQ ID NO: 1 does not function as a translation termination codon is preferably introduced to reverse the frameshift mutation. For example, an ilvG gene of the K12 strain may be replaced by the normal ilvG gene (SEQ ID NO: 3 or 5). Preferably, GT is inserted between the T at position 982 and the G at position 983 in SEQ ID NO: 1. This insertion may be achieved by site-directed mutagenesis using PCR.

Moreover, the nucleotides at position 982 to 984 of SEQ ID NO: 1 may be replaced with the nucleotides at position 982-986 from the normal ilvG gene (SEQ ID NO: 3) by P1 transduction. Furthermore, the full-length ilvG gene of the K12 strain may be replaced by the full-length normal ilvG gene.

Introducing the ilvG gene which does not have a frameshift mutation may be achieved by deleting one or four nucleotides in the region upstream of positions 982 to 984 of the ilvG gene to make the TGA out of frame. Specifically, the nucleotide C at position 979 may be deleted in SEQ ID NO: 1. Examples of such an ilvG gene include a gene having the nucleotide sequence of SEQ ID NO: 5.

Moreover, modification of a K12 strain so as to produce active AHASII may be performed by increasing the copy number of the normal ilvG gene (SEQ ID NO: 3) using genetic recombination techniques. In order to effectively increase the AHASII activity, an ilvM gene which encodes the small subunit of AHASII (for example, GenBank Accession No. X04890; 2374-2637) is also preferably introduced. The normal ilvG and ilvM genes may be introduced separately, but they may also be introduced simultaneously as normal ilvGM genes (for example, GenBank Accession No. X04890; 731-2637). Moreover, they may be introduced as the ilvGMEDA operon which contains a normal ilvG gene (for example, GenBank Accession No. X04890).

A gene which can be used for increasing the copy number of the normal ilvG gene may be one which hybridizes with the aforementioned normal ilvG gene (SEQ ID NO: 3 or 5 ) under stringent conditions as long as it encodes a protein that exhibits AHAS activity by forming a complex with an ilvM gene product. "Stringent conditions" as used herein are conditions under which a so-called specific hybrid is formed, and a non-specific hybrid is not formed. Examples of stringent conditions include, those under which DNAs having high homology hybridize to each other, for example, DNAs having a homology of not less than 70%, preferably not less than 80%, more preferably not less than 90%, especially preferably not less than 95%, hybridize to each other, and DNAs having homology lower than 70% do not hybridize to each other, and those under which DNAs hybridize to each other at a salt concentration with washing typical of Southern hybridization, i.e., washing once or preferably 2-3 times with 1×SSC, 0.1% SDS at 60° C., preferably 0.1×SSC, 0.1% SDS at 60° C., more preferably 0.1×SSC, 0.1% SDS at 68° C.

In order to introduce a normal ilvG gene (or ilvGM, ilvGMEDA gene), transformation can be performed as follows: a DNA fragment containing a nucleotide sequence of SEQ ID NO: 3 or SEQ ID NO: 5 is inserted into a vector which is able to replicate in a K-12 strain, preferably a multicopy vector, to thereby prepare a recombinant DNA. The recombinant DNA is then introduced into a K-12 strain. An example of a vector which is able to replicate in a K-12 strain includes a plasmid vector which is capable of autonomous replication in an *Escherichia coli*.

Examples of a vector which is capable of autonomous replication in an *Escherichia coli* K-12 strain include pUC19, pUC18, pHSG299, pHSG399, pHSG398, pACYC 184, (pHSG and pACYC are available from TAKARA BIO INC.), RSF 1010, pBR322, and pMW219 (pMW is available from NIPPON GENETIC Co., Ltd.).

Introducing a recombinant DNA which has been prepared as above into a K-12 strain or a derivative thereof may be performed by a known transformation method. Examples of transformation methods include treating recipient cells with calcium chloride so as to increase permeability of the DNA, which has been reported for *Escherichia coli* K-12 (Mandel, M. and Higa, A., J. Mol. Biol., 53, 159 (1970)), preparing competent cells from cells which are at growth phase, followed by transformation with DNA, which has been reported for *Bacillus subtilis* (Duncan, C. H., Wilson, G. A. and Young, F. E., Gene, 1, 153 (1977)), and so forth. In addition to these methods, introducing a recombinant DNA into protoplast- or spheroplast-like recipient cells, which have been reported to be applicable to *Bacillus subtilis*, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed. In addition, transformation of microorganisms can also be performed by the electric pulse method (JP2-207791 A).

The copy number of the normal ilvG can also be increased by integrating multiple copies of the normal ilvG gene into the chromosomal DNA of an *Escherichia coli* K12 strain. In order to integrate multiple copies of the gene into a chromosomal DNA of an *Escherichia coli* K 12 strain, homologous recombination (Experiments in Molecular Genetics, Cold Spring Harbor Lab., 1972) can be carried out by targeting a sequence which exists in multiple copies on a chromosomal DNA. Repetitive DNA and inverted repeats at the end of a transposon can be used as a sequence which exists in multiple copies on a chromosomal DNA. Alternatively, as disclosed in EP0332488B, it is also possible to incorporate the normal ilvG gene into a transposon, and allow it to be transferred so that multiple copies of the gene are integrated into the chromosomal DNA. Furthermore, the normal ilvG gene can also be incorporated into a host chromosome by using Mu phage (EP0332488B)

Enhancing expression of the normal ilvG gene can also be attained by replacing an expression regulatory sequence such as a promoter of the gene on a chromosomal DNA or on a plasmid with a stronger one, as disclosed in WO00/ 18935. For example, lac promoter, trp promoter, trc promoter, pL promoter, and so forth are known as strong promoters. Moreover, it is also possible to introduce several nucleotide substitutions into a promoter region of a gene so that the promoter is more potent. Substitution of the expression regulatory sequence can be performed, for example, in the same manner as a gene substitution using a temperature-sensitive plasmid. An example of a vector which has a temperature-sensitive replication origin for *Escherichia coli* includes plasmid pMAN997, which is described in WO99/03988, and so forth. Furthermore, substitution of an expression regulatory sequence can also be performed by using Red recombinase of λ phage (Datsenko, K. A., PNAS, 97(12), 6640-6645, 2000). Modification of an expression regulatory sequence can be combined with increasing a copy number of the gene. Furthermore, since it is known that a spacer sequence between the ribosome binding site (RBS) and translation initiation codon, especially, several nucleotides just upstream of the initiation codon, has a great influence on translation efficiency, this sequence may be modified. Expression regulatory sequences of the ilvG gene may be identified using a vector for promoter identification or genetic analysis software such as GENETYX.

The strain of the present invention is preferably a strain which shows improved growth substantially in the absence of branched-chain L-amino acids, when compared with a control strain (a parental strain including K12 strain), as a result of imparting L-valine resistance. In the present specification, the term "branched-chain L-amino acids" mean L-isoleucine, L-leucine, and L,-valine. In addition, the term "substantially in the absence of branched-chain L-amino acids" means a concentration of branched-chain L-amino acids in a medium of 1 g/L or less, preferably 100 mg/L or less, more preferably 50 mg/L or less, particularly preferably 0. Evaluation of growth of the strain imparted with L-valine resistance and the control strain substantially in the absence of branched-chain L-amino acids may be performed in both a liquid and a solid medium.

For example, a culture medium in which the L-valine resistant strain or a control strain has been cultured until the logarithmic growth phase or stationary phase is diluted with a medium, saline or the like, and the resultant bacterial cell suspension is applied on a solid medium not containing branched-chain L-amino acids, and these strains are cultured at an optimum growth temperature, for example, at 37° C. for 1 to 3 days. If the sizes of the emerging colonies of the L-valine resistant strains are larger than those of the control strain, it is considered that the growth of the L-valine resistant strain is better than that of the control strain. The amount of the branched-chain L-amino acids to be added to a solid medium is, for example, 50 mg/L or less, preferably 10 mg/L or less, more preferably 0.

Alternatively, a bacterial cell suspension of an L-valine-resistant strain or a control strain that has been cultured and diluted as described above can be inoculated into a liquid medium substantially in the absence of branched-chain L-amino acids, and cultured at optimum growth temperature, for example, at 37° C. for about several hours to 1 day, preferably for about 6 hours. The amount of a branched-chain L-amino acid to be added to the medium is, for example, 50 mg/L or less, more preferably 10 mg/L or less, preferably 0. If the optical density (OD) or turbidity of the L-valine-resistant strain is higher than that of the control strain at either the logarithmic growth phase or stationary phase, it is considered that the growth of the L-valine-resistant strain is better than that of the control strain. It is also considered that the growth of the L-valine-resistant strain is better if the strain reaches the logarithmic growth phase or the maximum value of OD earlier than the control strain. The aforementioned term "logarithmic growth phase" refers to a stage when cell numbers logarithmically increase. Meanwhile, the term "stationary phase" refers to the stage when no increase in cell number is observed because division and proliferation are stopped after the logarithmic growth phase.

The strain of the present invention can be obtained by imparting an ability to the above-described L-valine resistant strain to produce one or more L-amino acids selected from the group consisting of L-tryptophan, L-phenylalanine, L-lysine, L-tyrosine, L-glutamic acid, L-histidine, L-cysteine, and L-proline. Alternatively, an ability to produce the L-amino acids may be imparted first, followed by imparting L-valine resistance.

In the present invention, the term "ability to produce the L-amino acids" refers to an ability to produce and cause accumulation of the L-amino acids in a medium or a bacterial cell when the strain of the present invention is cultured in the medium. A strain which has an ability to produce the L-amino acids may be one which originally has an ability to produce the L-amino acid, or one which has been modified to have an ability to produce the L-amino acid by using a mutation method or a recombinant DNA technique. The strain of the present invention may be one to which an ability to produce the L-amino acids is imparted by enhancing the expression of the aforementioned normal ilvG gene. The strain of the present invention may have an ability to produce two or more kinds of L-amino acids selected from the group consisting of L-tryptophan, L-phenylalanine, L-lysine, L-tyrosine, L-glutamic acid, L-histidine, L-cysteine, and L-proline.

In order to impart an ability to produce the L-amino acids, methods conventionally adopted in the breeding of an L-amino acid producing microorganism including coryneform bacterium and *Escherichia* bacterium can be used. For example, these methods include creating an auxotrophic mutant strain, analogue resistant strain, or metabolic regulation mutant strain, and creating a recombinant strain in which the activity of an L-amino acid biosynthetic enzyme is enhanced (see Amino Acid Fermentation, p. 77 to 100, Japan Scientific Societies Press, first edition publication: May 30, 1986). In the present invention, an auxotrophic mutation, an analogue resistant mutation, and a metabolic regulation mutation may be introduced singly or in combination during breeding of an L-amino acid-producing strain. Furthermore, activities of two or more kinds of L-amino acid biosynthetic enzymes may be enhanced. Furthermore, introduction of an auxotrophic mutation, an analogue resistant mutation, and a metabolic regulation mutation may be combined with enhancement of activity of an L-amino acid biosynthetic enzyme.

An auxotrophic mutant strain, analogue resistant strain, and metabolic regulation mutant strain which have an ability to produce an L-amino acid can be obtained as follows. A K12 strain or derivative thereof is treated by a general mutation treatment, i.e., irradiation with X-ray or ultraviolet ray or by a treatment with a mutagen such as N-methyl-N'-nitro-N-nitrosoguanidine, and a strain that exhibits auxotrophy, analogue resistance, or metabolic regulation mutation and has an ability to produce an L-amino acid is selected from the resulting mutant strains.

Hereinafter, examples of strains derived from a K12 strain and which have L-amino acid-producing ability will be described. Therefore, L-valine resistance may be imparted to the following strains. However, L-amino acid-producing strains are not limited to the following.

As a strain having L-tryptophan-producing ability, a bacterium in which one or more activities of the enzymes selected from anthranilate synthase, phosphoglycerate dehydrogenase, and tryptophan synthase are enhanced can be used. The anthranilate synthase and phosphoglycerate dehydrogenase are both subject to feedback inhibition by L-tryptophan and L-serine, so that a mutation desensitizing the feedback inhibition may be introduced into these enzymes. Specifically, for example, anthranilate synthase gene (trpE) and/or phosphoglycerate dehydrogenase gene (serA) is mutated so as not to be subject to feedback inhibition, and the resulting mutant gene is introduced into a K12 strain or its derivative. Specific examples of such a strain include a *Escherichia coli* SV164 strain which harbors desensitized anthranilate synthase and a transformant strain obtained by introducing into the *Escherichia coli* SV164 strain the plasmid pGH5 (see WO 94/08031), which contains a mutant serA gene encoding feedback-desensitized phosphoglycerate dehydrogenase.

A strain into which a recombinant DNA containing a tryptophan operon is introduced is also preferably used as an L-tryptophan-producing strain. Specific examples thereof include an *Escherichia coli* strain into which a tryptophan operon which contains a gene encoding desensitized anthranilate synthase has been introduced (JP-A 57-71397, JP-A 62-244382, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by trpA and trpB, respectively.

Examples of L-phenylalanine-producing strains include an *E. coli* strain AJ12739 (tyrA::Tn10, tyrR); an *E. coli* strain HW1089 (ATCC Accession No. 55371) harboring pheA34 gene (U.S. Pat. No. 5,354,672); a mutant MWEC101-b strain (KR8903681); strains NRRL B-12141, NRRL B-12145, NRRL B-12146 and NRRL B-12147 (U.S. Pat. No. 4,407,952) and the like. Examples of L-phenylalanine-producing strains further include an *E. coli* strain K-12 [W3110 (tyrA)/pPHAB], an *E. coli* strain K-12 [W3110 (tyrA)/pPHAD], an *E. coli* strain K-12 [W3110 (tyrA)/pPHATerm] and an *E. coli* strain K-12 [W3110 (tyrA)/pBR-aroG4,pACMAB] named AJ 12604, and the like (European patent EP488424B1), and a strain in which yddG gene and yedA gene which are involved in phenylalanine excretion, are amplified (WO 03/044192).

Examples of L-tyrosine-producing include *E. coli* strains wherein phosphoenolpyruvate-producing ability or enzymatic activity of the common aromatic pathway is enhanced (EP0877090A) and the like. Genes effective for aromatic amino acids' biosynthesis include genes of a common pathway for aromatic acids, such as aroF, aroG, aroH, aroB, aroD, aroE, aroK, aroL, aroA, and aroC genes.

Furthermore, examples of L-tryptophan-producing strains include a strain auxotrophic for L-phenylalanine and L-tyrosine (*Escherichia coli* AGX17(pGX44) [NRRL B-12263] strain), and a strain which harbors a plasmid pGX50 containing a tryptophan operon (AGX6(pGX50)aroP [NRRL B-12264] strain) (see U.S. Pat. No. 4,371,614).

Examples of L-lysine-producing strains include *Escherichia coli* AJ11442 strain (FERM BP-1543, NRRL B-12185; see JP 56-18596 A and U.S. Pat. No. 4,346,170) and *Escherichia coli* VL611 strain (JP 2000-189180 A). Moreover, WC 196 strain (see WO 96/17930) may also be used as L-lysine-producing strain. WC196 strain is obtained by imparting AEC (S-(2-aminoethyl)-cysteine) resistance to the W3110 strain, which is derived from *Escherichia coli* K-12. The strain was named *Escherichia coli* AJ13069 strain and was deposited at the National Institute of Bioscience and Human-Technology, Agency of Industrial Science and Technology, Ministry of International Trade and Industry (currently, National Institute of Bioscience and Human-Technology, National Institute of Advanced Industrial Science and Technology; 1-3, Higashi 1-Chome, Tsukuba-shi, Ibaraki-ken, 305-8566, Japan) on Dec. 6, 1994 and given an accession number of FERM P-14690. The deposit was then converted to an international deposit under the provisions of Budapest Treaty on Sep. 29, 1995 and given an accession number of FERM BP-5252.

Examples of L-histidine-producing strains include *Escherichia coli* strains transformed with a vector which contains a gene encoding L-histidine biosynthetic enzyme (FERM-P 5038, FERM-P 5048; JP 56-005099A), a strain into which the rht gene, an amino acid excretion gene, is introduced (EP 1016710 A), and *Escherichia coli* 80 strain resistant to sulfaguanidine, D,L-1,2,4-triazole-3-alanine, and streptomycin (VKPM B-7270, Russian Patent 2119536).

As an L-cysteine-producing strain derived from *Escherichia coli* K-12 strain, a strain which has a decreased cystathionine-β-lyase activity (JP 2003-169668A), and a strain harboring serine acetyltransferase desensitized to feedback inhibition by L-cysteine (JP-A 11-155571), etc. may be used.

As an L-proline-producing strain derived from *Escherichia coli* K-12 strain, the 702 strain that is resistant to 3,4-dehydroxy proline and azatidine-2-carboxylate (VKPMB-8011) and the 702ilvA strain (VKPMB-8012 strain) which is obtained by disrupting the ilvA gene in the 702 strain may be used (JP 2002-300874A).

*Escherichia coli* having an ability to produce L-glutamic acid can also be obtained by enhancing the activity of an L-glutamic acid biosynthetic enzyme. Examples of L-glutamic acid biosynthetic enzymes include glutamate dehydrogenase, glutamine synthetase, glutamate synthase, isocitrate dehydrogenase, aconitate hydratase, citrate synthase, pyruvate carboxylase, phosphoenolpyruvate carboxylase, phosphoenolpyruvate synthase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase, and so forth.

*Escherichia coli* having an ability to produce L-glutamic acid can also be obtained by reducing or eliminating an activity of one or more enzymes which catalyze a reaction causing a branching from L-glutamic acid synthesis and producing a compound other than L-glutamic acid. Such enzymes include isocitrate lyase, α-ketoglutarate dehydrogenase, phosphate acetyltransferase, acetate kinase, acetohydroxy acid synthase, acetolactate synthase, formate acetyltransferase, lactate dehydrogenase, glutamate decarboxylase, 1-pyrophosphate dehydrogenase, and so forth. Specifically, examples of *Escherichia coli* in which α-ketoglutarate dehydrogenase activity is reduced include *Escherichia coli* strains disclosed in JP5-244970A or JP7-203980A.

<2> Method of Producing L-amino Acids

The L-amino acids selected from the group consisting of L-tryptophan, L-phenylalanine, L-lysine, L-tyrosine, L-glutamic acid, L-histidine, L-cysteine, and L-proline can be produced by culturing the *Escherichia coli* strain as obtained above in a medium to produce and cause accumulation of the L-amino acids in the medium or in the bacterial cells; and collecting the L-amino acids from the medium or bacterium cells. Growth of the strain of the present invention is improved when substantially in the absence of branched-chain L-amino acids, so that the L-amino acids can be effectively produced even when substantially in the absence of branched-chain L-amino acids.

The strain of the present invention can be cultured in a medium that has been conventionally used in fermentative production of an L-amino acid. That is, a general medium containing a carbon source, a nitrogen source, an inorganic ion, and if necessary, other organic components can be used. Examples of carbon sources include: saccharides such as glucose, sucrose, lactose, galactose, fructose, and starch hydrolysate; alcohols such as glycerol and sorbitol; and organic acids such as fumaric acid, citric acid, and succinic acid. Examples of nitrogen sources include: inorganic ammonium salts such as ammonium sulfate, ammonium chloride and ammonium phosphate; organic nitrogen substances such as a soybean hydrolysate; ammonia gas; and aqueous ammonia. As trace amounts of organic nutrients, auxotrophic nutrients such as vitamin B1 and L-homoserine, yeast extracts, and the like can be preferably added in an appropriate amount. Other than such substances, if necessary, potassium phosphate, magnesium sulfate, iron ion, manganese ion, or the like is added in a small amount. The medium to be used in the present invention may be a natural or a synthetic medium as long as it is a medium which contains a carbon source, nitrogen source, inorganic ions, and if necessary, other organic nutrients.

The culture is preferably performed under aerobic conditions for 1 to 7 days. The culture temperature is preferably 24° C. to 37° C., and the pH is 5 to 9. pH can be adjusted using an inorganic or organic acidic or alkaline substance as well as ammonia gas or the like. L-amino acids can be collected the fermentation liquor by methods which include the ion-exchange resin method, precipitation method, and the like. In the case where L-amino acids are accumulated in a bacterial cell, L-amino acids can be collected, for example, by disrupting bacterial cells by ultrasonication and removing the bacterial cells by centrifugation, followed by collection using an ion-exchange resin method or the like.

EXAMPLES

Hereinafter, the present invention will be described in more detail referring to the following non-limiting examples.

Reference Example 1

Using the L-tryptophan-producing strain SV164/pGH5, the effect of the addition of branched-chain L-amino acids on accumulation of L-tryptophan was investigated.

The SV164/pGH5 strain is an L-tryptophan-producing strain which is obtained by introducing the plasmid pGH5 which contains a mutant serA gene encoding a feedback-desensitized phosphoglycerate dehydrogenase (see WO 94/08031) into the SV164 strain. The SV164 strain (JP 3032013 B) is a strain which is obtained by introducing a mutation into an allelic gene of the TrpE gene which encodes anthranilate synthase in YMC9 strain (ATCC 33927), which is a strain derived from the K12 strain.

Predetermined amounts of L-isoleucine and L-leucine were added to a medium for L-tryptophan production (40 g/L glucose, 1.5 g/L KH$_2$PO$_4$, 0.5 g/L NaCl, 15 g/L (NH$_4$)$_2$SO$_4$, 0.3 g/L MgSO$_4$.7H$_2$O, 14.7 mg/L CaCl$_2$.2H$_2$O, 75 mg/L FeSO$_4$.7H$_2$O, 0.15 mg/L Na$_2$MoO$_4$.7H$_2$O, 0.7 mg/L CoCl$_2$.7H$_2$O, 1.6 mg/L MnCl$_2$.7H$_2$O, 2.5 mg/L H$_3$BO$_3$, 0.25 mg/L CuSO$_4$.7H$_2$O, 0.3 mg/L ZnSO$_4$.7H$_2$O, 1 g/L Na$_3$Citrate, 125 mg/L L-phenylalanine, 125 mg/L L-Tyr, 5 mg/L thiamine.HCl, 1 g/L yeast extract, 2 g/L Corn steep solid, 30 g/L CaCO$_3$, 20 mg/L tetracycline, pH 7.1 (NH$_4$OH)), and the SV164/pGH5 strain was cultured for 40 hours. The residual sugar, the accumulated amount of L-tryptophan, and the yield of L-tryptophan per sugar consumption are shown in Table 1.

TABLE 1

Effect of addition of L-isoleucine (Ile) and L-leucine (Leu) on L-tryptophan (Trp) accumulation

| Yeast Extract added (g/L) | Ile, Leu added (mg/L) | OD562 (×26) | Residual sugar (g/L) | Accumulated of Trp (g/L) | Yield per sugar (%) |
|---|---|---|---|---|---|
| 0.1 | 0 | 0.18 | 16.2 | 3.4 | 16.3 |
| 0.1 | 0 | 0.165 | 16.3 | 3.22 | 15.5 |
| 0.1 | 50 | 0.215 | 7.86 | 4.99 | 17.1 |
| 0.1 | 50 | 0.227 | 7.34 | 4.5 | 15.2 |
| 0.1 | 50 | 0.232 | 6.62 | 4.71 | 15.5 |
| 0.1 | 50 | 0.229 | 7.14 | 4.82 | 16.1 |
| 0.1 | 100 | 0.32 | 0.34 | 4.95 | 13.5 |
| 0.1 | 100 | 0.342 | 0.34 | 5.81 | 15.9 |
| 0.3 | 50 | 0.295 | 0.34 | 5.81 | 15.6 |
| 0.3 | 50 | 0.316 | 0.32 | 6.03 | 16.2 |

The results revealed that the growth, sugar consumption, and amount of produced L-tryptophan from the SV164/pGH5 strain decreased when L-isoleucine and L-leucine are not added.

Example 1

Acquisition and Evaluation of the L-valine Resistant Strain (1-1) Acquisition of the L-valine Resistant Strain L-valine resistance was introduced by P1 transduction. M1162 strain (Lawther et al., J. Bacteriol., 149, 294- (1982)) and TDH7 strain (EP-0593792-B1, VKPM B-5318) were used as a donor strain for the L-valine resistance. The mutation in the M1162 strain which relates to valine resistance resides in the ilvG gene, which has been identified as ilvG603. The ilvG gene of MI162 strain is shown in SEQ ID NO: 3, and the frameshift mutation observed in the ilvG gene of the K12 strain has been reversed. Meanwhile, TDH7 is mutated so that the C at position 979 of SEQ ID NO: 1 is deleted, and the frameshift mutation observed in the ilvG gene of the K12 strain has been reversed. The ilvG gene of the TDH7 strain is shown in SEQ ID NO: 5. The above-described SV164/pGH5 strain was used as a recipient strain.

In accordance with a conventional method, a P1 transduction experiment was performed. Each bacterium was applied to a minimum medium containing L-valine (4 g/L glucose, 12.8 g/L Na$_2$HPO$_4$.7H$_2$O, 3 g/L KH$_2$PO$_4$, 0.5 g/L NaCl, 1 g/L NH$_4$Cl, 5 mM MgSO$_4$, 0.1 mM CaCl$_2$, 1 mg/L thiamine, 20 mg/l L-phenylalanine, 20 mg/L L-tyrosine, 20 mg/L L-methionine, 3 mg/L pyridoxine, 20 mg/L L-valine, 20 mg/L tetracycline), followed by culture at 37° C. for 3 days. Then, the colonies which emerged were selected as L-valine resistant strains.

The following analysis was performed using the three kinds of L-valine resistant strains, that is, M6 and M9 strains which were obtained with MI162 strain as a donor and T2 strain obtained with TDH7 strain as a donor.

(1-2) The Effect of Addition of L-isoleucine and L-leucine on L-tryptophan Accumulation of the L-valine Resistant Strains Using the obtained L-valine resistant strains and the parental strain (SVI164/pGH5 strain), the effect of addition of L-isoleucine and L-leucine on their L-tryptophan-producing ability was investigated. Each strain was cultured at 30° C. for 24 hours in an LB medium plate (10 g/L polypeptone, 5 g/L yeast extract, 10 g/L NaCl, 20 mg/L tetracycline, 20 g/L agar), and the colony which appeared was inoculated into a test tube containing 4 ml of LB medium, followed by culture at 30° C. for 24 hours with shaking. Each culture was seeded in a sakaguchi flask (volume: 500 ml) containing 40 ml of a producing medium (40 g/L glucose, 1.5 g/L $KH_2PO_4$, 0.5 g/L NaCl, 15 g/L $(NH_4)_2SO_4$, 0.3 g/L $MgSO_4.7H_2O$, 14.7 mg/L $CaCl_2.2H_2O$, 75 mg/L $FeSO_4.7H_2O$, 0.15 mg/L $Na_2MoO_4.7H_2O$, 0.7 mg/L $CoCl_2.7H_2O$, 1.6 mg/L $MnCl_2.7H_2O$, 2.5 mg/L $H_3BO_3$, 0.25 mg/L $CuSO_4.7H_2O$, 0.3 mg/L $ZnSO_4.7H_2O$, 1 g/L $Na_3Citrate$, 30 mg/L pyridoxine, 50 mg/L L-methionine, 125 mg/L L-phenylalanine, 125 mg/L L-Tyr, 5 mg/L thiamine.HCl, 1 g/L yeast extract, 2 g/L Corn steep solid, 30 g/L $CaCO_3$, 20 mg/L tetracycline, pH 7.1 ($NH_4OH$)), followed by culture with shaking at 30° C. for 40 hours. After the culture, L-tryptophan accumulation of each strain was analyzed (FIG. 1).

In the control strain (SV164/pGH5 strain), the accumulated L-tryptophan was found to be low when L-isoleucine and L-leucine were not added, while in each of the L-valine resistant strains (M6, M9, and T2), the amount of L-tryptophan which accumulated when L-isoleucine and L-leucine were not added was found to be almost the same as when L-isoleucine and L-leucine were added.

Figure 2:
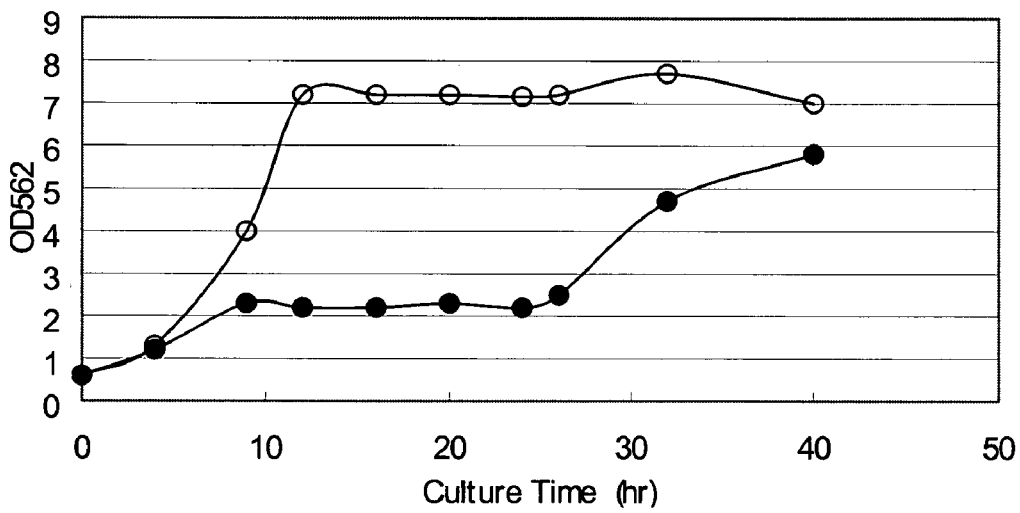
FIG. 2 shows the growth of the SV164/pGH5 strain and an L-valine-resistant strain (T2) when L-leucine and L-isoleucine have not been added. The symbols ● and ○ represent the SV164/pGH5 and T2 strains, respectively.

Furthermore, growth of the obtained L-valine resistant strain (T2 strain) and the control strain in a minimum medium without branched-chain L-amino acids (L-isoleucine and L-leucine) was investigated in detail. SV164/pGH5 strain or T2 strain was inoculated in a minimum medium (4 g/L glucose, 12.8 g/L $Na_2HPO_4.7H_2O$, 3 g/L $KH_2PO_4$, 0.5 g/L NaCl, 1 g/L $NH_4Cl$, 5 mM $MgSO_4$, 0.1 mM $CaCl_2$, 1 mg/L thiamine, 20 mg/L tetracycline) to which 20 mg/L of each amino acid other than L-isoleucine, L-leucine, L-valine and L-tryptophan was added, followed by culture with shaking at 30° C. Then, the growth of each strain was monitored by measuring OD660 with time (FIG. 2). As a result, growth of the SV164/pGH5 strain was delayed in a medium containing L-isoleucine, L-leucine or L-valine, whereas growth of the L-valine resistant strain (T2 strain) was not delayed, which suggested that the lack of a branched-chain L-amino acid during growth was reduced in the L-valine resistant strain. The results show that L-amino acids including L-tryptophan can be effectively produced by using a K12 derived strain imparted with L-valine resistance without adding branched-chain L-amino acids.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP2004-130088, is incorporated by reference herein in its entirety.

INDUSTRIAL APPLICABILITY

The strains of the present invention can grow well substantially in the absence of branched-chain L-amino acids. Accordingly, when the strains of the present invention are used, L-amino acids such as L-tryptophan, L-phenylalanine, L-lysine, L-tyrosine, L-glutamic acid, L-histidine, L-cysteine, and L-proline can be effectively produced even substantially in the absence of branched-chain L-amino acid.

---

We claim:

1. A method for producing an L-amino acid selected from the group consisting of L-tryptophan, L-phenylalanine, L-lysine, L-tyrosine, L-glutamic acid, L-histidine, L-cysteine, and L-proline, comprising culturing in a medium a modified *Escherichia coli* K12 strain, MG1655 strain, W3110 strain, or SV164 strain, wherein said strain has an ability to grow in a medium containing 20 mg/L of L-valine, and collecting said L-amino acid from the medium or the strain, wherein said strain is modified so as to produce active acetohydroxy acid synthase II, wherein said active acetohydroxy acid synthase II is encoded by the *E. coli* ilvG gene in which a mutation is made at one or more positions corresponding to positions 982 to 984 of SEQ ID NO: 1 or at one or more positions upstream of these positions, wherein said mutation results in a frameshift of said ilvG gene.

2. The method according to claim 1, wherein said active acetohydroxy acid synthase II is encoded by a gene comprising a nucleotide sequence of SEQ ID NO: 3 or 5.

3. The method according to claim 1, wherein said amino acid is L-tryptophan.

4. The method according to claim 1, wherein said amino acid is L-phenylalanine.

5. The method according to claim 1, wherein said amino acid is L-L-lysine.

6. The method according to claim 1, wherein said amino acid is L-tyrosine.

7. The method according to claim 1, wherein said amino acid is L-glutamic acid.

8. The method according to claim 1, wherein said amino acid is L-histidine.

9. The method according to claim 1, wherein said amino acid is L-cysteine.

10. The method according to claim 1, wherein said amino acid is L-proline.

11. The method according to claim 2, wherein said amino acid is L-tryptophan.

12. The method according to claim 2, wherein said amino acid is L-phenylalanine.

13. The method according to claim 2, wherein said amino acid is L-L-lysine.

14. The method according to claim 2, wherein said amino acid is L-tyrosine.

15. The method according to claim 2, wherein said amino acid is L-glutamic acid.

16. The method according to claim 2, wherein said amino acid is L-histidine.

17. The method according to claim 2, wherein said amino acid is L-cysteine.

18. The method according to claim 2, wherein said amino acid is L-proline.

19. The method according to claim 1, wherein said strain is modified so as to produce active acetohydroxy acid synthase II by increasing the copy number of said gene.

20. The method according to claim 2, wherein said strain is modified so as to produce active acetohydroxy acid synthase II by increasing the copy number of said gene.

* * * * *